United States Patent [19]

Houlihan

[11] 4,219,560
[45] Aug. 26, 1980

[54] PIPERIDINE AND PYRROLIDINE ALCOHOLS

[75] Inventor: William J. Houlihan, Mt. Lakes, N.J.

[73] Assignee: Sandoz, Inc., E. Hanover, N.J.

[21] Appl. No.: 896,896

[22] Filed: Apr. 17, 1978

Related U.S. Application Data

[63] Continuation-in-part of Ser. No. 862,404, Dec. 20, 1977, abandoned.

[51] Int. Cl.² .................. C07D 405/04; A61K 31/40; A61K 31/445
[52] U.S. Cl. ................................. 424/267; 424/248.4; 424/248.57; 424/248.58; 424/250; 424/274; 544/129; 544/141; 544/360; 544/372; 546/186; 546/191; 546/197; 546/208; 546/240; 260/326.5 CA; 260/326.5 G; 260/326.5 R; 260/326.85
[58] Field of Search .............. 546/197; 260/326.5 CA; 424/267, 274

[56] References Cited
U.S. PATENT DOCUMENTS 3,982,001 9/1976 Heffe et al. ............... 546/197

Primary Examiner—Henry R. Jiles
Assistant Examiner—R. W. Ramsuer
Attorney, Agent, or Firm—Gerald D. Sharkin; Robert S. Honor; Timothy G. Rothwell

[57] ABSTRACT

This disclosure describes novel compounds of the formula:

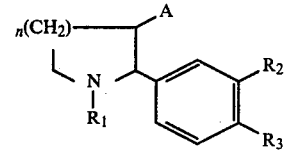

where A is —CH₂OH or

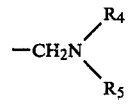

wherein $R_4$ and $R_5$ each independently represent hydrogen or lower alkyl having 1 to 2 carbon atoms or together with N represent

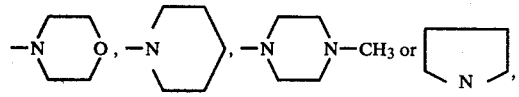

and,
$R_1$ is hydrogen or lower alkyl having 1 to 2 carbon atoms, and
$R_2$ and $R_3$ each independently represent hydrogen, chloro, fluoro, methyl, methoxy or together, represent methylenedioxy, and
n is 1 or 2, provided that one of $R_2$ and $R_3$ is other than hydrogen which are useful as hypolipidemic agents.

9 Claims, No Drawings

PIPERIDINE AND PYRROLIDINE ALCOHOLS

This application is a continuation-in-part of copending application Ser. No. 862,404, filed Dec. 20, 1977 now abandoned.

This invention relates to substituted piperidine and pyrrolidine alcohols and amines which exhibit hypolipidemic activity. In particular, it relates to substituted piperidine and pyrrolidine alcohols and amines, intermediates thereof and pharmaceutically acceptable acid addition salts.

The compounds of this invention may be represented by the following structural formula:

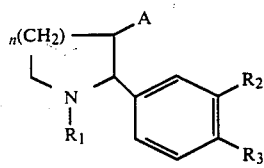
(I)

where A is —CH$_2$OH or

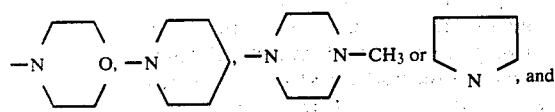

wherein R$_4$ and R$_5$ each independently represent hydrogen or lower alkyl having 1 to 2 carbon atoms or together with N represent

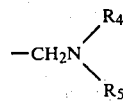

R$_1$ is hydrogen or lower alkyl having 1 to 2 carbon atoms ie. methyl or ethyl, and R$_2$ and R$_3$ each independently represent hydrogen, fluoro, chloro, methyl, methoxy or together represent methylenedioxy, and n is 1 or 2, provided that one of R$_2$ and R$_3$ is other than hydrogen.

The compounds of formula (I) in which

A is

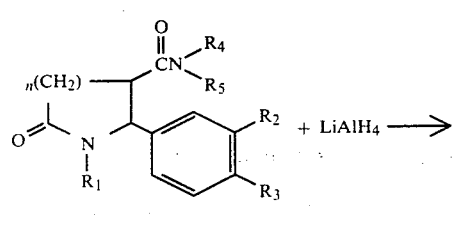
(II)

are prepared according to the following reaction scheme.

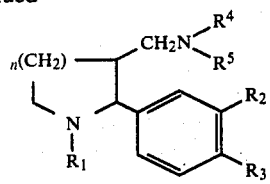
(Ia)

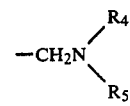

where R$_1$, R$_2$, R$_3$, R$_4$, R$_5$, n and the proviso are as defined above.

The compounds of formula (Ia) are prepared by reducing a compound of the formula (II) with lithium aluminum hydride, in the presence of an inert atmosphere e.g. nitrogen, helium or argon, preferably nitrogen and in the presence of an inert organic solvent. Although the particular solvent employed is not critical, the preferred solvents include the ethers such as diethylether, tetrahydroforan and the like, preferably tetrahydrofuran. The temperature of the reaction is not critical but it is preferred that the reaction be run from about 25° to 50° C., preferably the reflux temperature of the solvent. The reaction is run from about 12 to 48 hours preferably from about 24 to 36 hours. The product is recovered using conventional techniques e.g. distillation.

The compounds of formula (II) are prepared in accordance with the following reaction scheme:

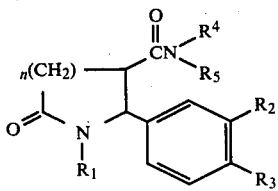

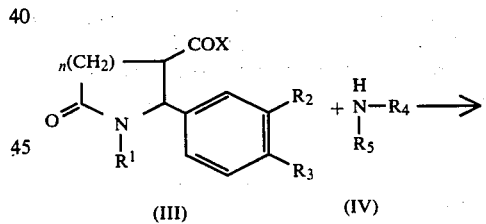
(II)

where X is chlorine or bromine, and R$_1$, R$_2$, R$_3$, R$_4$, R$_5$, n and the proviso are as defined above.

The compounds of formula (II) are prepared by reacting a compound of the formula (III) with a compound of the formula (IV) in the presence of an inert organic solvent. Although the particular solvent employed is not critical, the preferred solvents include the ethers such as diethylether or tetrahydrofuran, the latter being especially preferred. The temperature of the reaction is not critical, but it is preferred that the reaction be carried out at a temperature of from about 15° to 45° C. preferably from about 20° to 30° C. The reaction is run from about 6 to 24 hours, preferably from about 8 to 14 hours. The product is recovered using conventional techniques e.g. filtration.

The compounds of formula (III) are prepared according to the following reaction scheme.

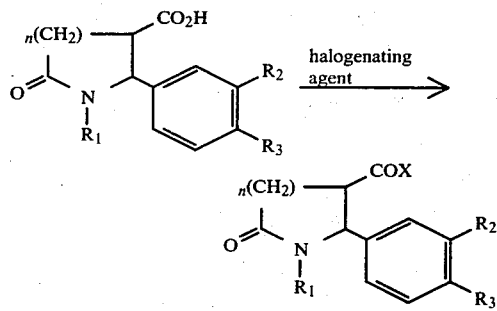

where X, $R_1$, $R_2$, $R_3$, n and the proviso are as defined above.

The compounds of formula (III) are prepared by treating a compound of the formula (V) with a halogenating agent such as phosphorous oxychloride, phosphorous pentachloride, thionyl chloride, thionyl bromide, preferably thionyl chloride in the presence of an inert organic solvent. Although the particular solvent employed is not critical, the preferred solvents include the halogenated hydrocarbons such as methylene chloride, chloroform and the like or an excess of the halogenating agent utilized above, the latter being especially preferred. The temperature of the reaction is not critical, but it is preferred that the reaction be run from about 15° to 45° C., preferably from about 20° to 30° C. The reaction is run from about about 12 to 36 hours, preferably from about 18 to 24 hours. The compounds of formula (III) may be recovered using conventional techniques. However it is preferred that it be employed in situ in the preparation of compounds (II).

The compounds of formula (V) are prepared in accordance with the following reaction scheme:

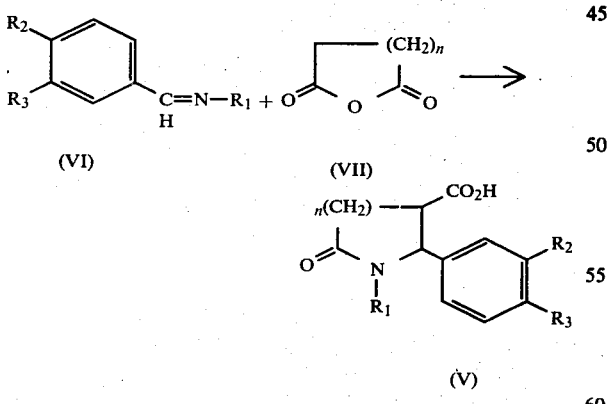

where $R_1$, $R_2$, $R_3$, n and the proviso are as defined above.

The compounds of formula (V) are prepared by treating a compound of the formula (VI) with a compound of the formula (VII) in the presence of an inert organic solvent. Although the particular solvent employed is not critical, the preferred solvents include the aromatic hydrocarbons such as toluene, xylene and the like, the aromatic halides such as chlorotoluene, chloroxylene, dichlorobenzene and the like, preferably xylene. The reaction should be carried out at a temperature above 100° C., and it is preferred that the reaction be run from about 120° to 150° C., preferably the reflux temperature of the solvent. The reaction is run from about 2 to 18 hours, preferably from about 3 to 6 hours. The product is recovered using conventional techniques, e.g., filtration.

The compounds of formula (VI) are prepared according to the following reaction scheme:

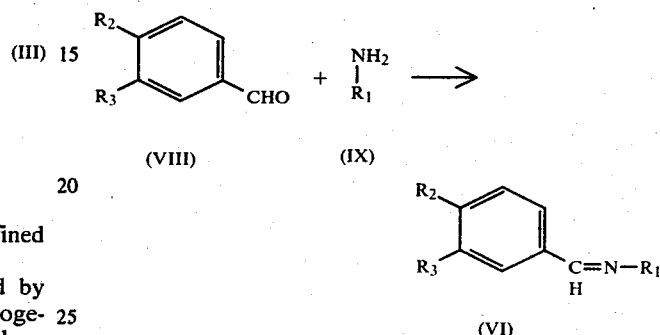

where $R_1$, $R_2$, $R_3$ and the proviso are as defined above.

The compounds of formula (VI) are prepared by treating a compound of the formula (VIII) with a compound of the formula (IX) in the presence of a water binding agent, preferably molecular seives and an inert organic solvent. Although the particular solvent employed is not critical, the preferred solvents include the aromatic hydrocarbons such as benzene, toluene, xylene and the like, preferably toluene. The temperature of the reaction is not critical, but it is preferred that the reaction be run from about 10° to 45° C., preferably from about 20° to 30° C. The reaction is run from about 8 to 48 hours, preferably from about 12 to 24 hours. The product is recovered using conventional techniques, e.g., filtration.

The compounds of formula (I) in which A is $-CH_2OH$ are prepared according to the following reaction scheme:

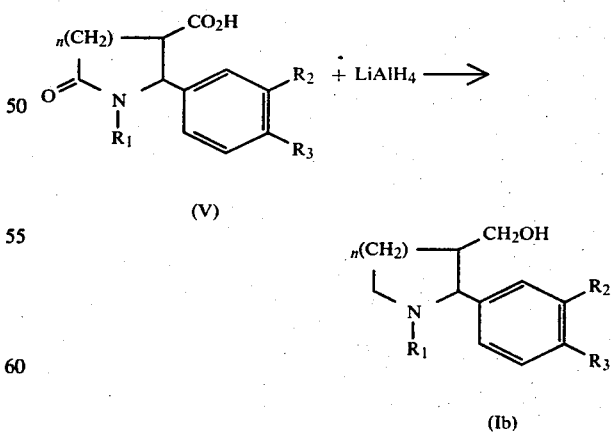

where $R_1$, $R_2$, $R_3$, $R_4$, $R_5$, n and the proviso are as defined above.

The compounds of formula (Ib) are prepared by reducing a compound of the formula (V) with lithium aluminum hydride, in the presence of an inert atmosphere, e.g., nitrogen, helium or argon, preferably nitrogen in the presence of an inert organic solvent. Although the particular solvent employed is not critical, the preferred solvents include the ethers such as diethylether, tetrahydrofuran and the like, preferably tetrahydrofuran. The temperature of the reaction is not critical, but it is preferred that the reaction be run from about 20° to 60° C., preferably the reflux temperature of the solvent. The reaction is run from about 18 to 40 hours, preferably from about 25 to 35 hours. The product is recovered using conventional techniques, e.g., filtration.

The compounds of formulae (IV), (VII), (VIII) and (IX) are known and may be prepared by methods described in the literature. The compounds of formulae (IV), (VII), (VIII) and (IX) not specifically described may be prepared by analogous methods from known starting materials.

It will be understood that the compounds of formulae (Ia) and (Ib) may exist in the form of optically active isomers, and also in the form of geometric isomers which can be separated and recovered by conventional techniques, and such isomeric forms are included within the scope of this invention.

The compounds of formulae (Ia) and (Ib) are useful because they possess pharmacological activity in animals. In particular, the compounds are useful as hypolipidemic agents in the treatment of lipidemia as indicated by the fall in cholesterol and/or triglyceride levels in male albino Wistar rats weighing 110-130 g. initially. The rats are maintained on drug-free laboratory chow diet for seven days and then divided into groups of 6 to 10 animals. Each group, with the exception of the control, is then given orally 120 to 500 milligrams per kilogram of body weight per diem of the test compound for six days. At the end of this period, the animals are anesthetized with sodium hexobarbital and bled from the carotid arteries. Serum or plasma samples are collected and 1.0 ml. of the serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium Mediad Inc., New York, 345-347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

When the compounds are employed for the above utility, they may be combined with one or more pharmaceutically acceptable carriers or adjuvants and may be administered orally in such forms as tablets, capsules, dispersible powders, granules, syrups, elixirs, suspensions, and the like, or parenterally in the form of sterile injectable solutions or suspensions. These pharmaceutical preparations may contain up to about 90° of the active ingredient in combination with the carrier or adjuvant. Furthermore, the compounds of formula (Ia) and (Ib) may be similarly administered in the form of their non-toxic pharmaceutically acceptable acid addition salts. Such salts possess the same order of activity as the free base, are readily prepared by reacting the base with an appropriate acid, and, accordingly, are included within the scope of the invention. Representative of the acid addition salts are the neutral acid salts such as the hydrochloride, hydrobromide sulfate, phosphate and the like, and the organic salts such as succinate, benzoate, acetate, and the like.

The hypolipidemic effective dosage of active ingredient employed for the treatment of lipidemia may vary depending on the particular compound employed, the mode of administration and the severity of the condition being treated. However, in general, satisfactory results are obtained when the compounds of formula (I) are administered at a daily dosage of from about 3 milligrams to about 250 milligrams per kilogram of animal body weight, preferably given in divided doses two to four times a day, or in sustained release form. For most large mammals, the total daily dosage is from about 200 to about 1000 milligrams. Dosage forms suitable for internal use comprise from about 50 to 500 milligrams of the active compound in intimate admixture with a solid or liquid pharmaceutically acceptable carrier or diluent.

A representative formulation suitable for oral administration is a capsule prepared by standard encapsulating techniques which contain the following and may be administered two to four times a day in the treatment of lipidemia.

| INGREDIENT | WEIGHT (mg.) |
|---|---|
| 1-methyl-2-(3,4-methylenedioxyphenyl)-3-piperidinemethanol | 150 |
| Inert filler (starch, lactose, kaolin, etc.) | 300 |

EXAMPLE 1.

Piperonal-N-methylimine.

To a flask equipped with stirrer, condenser and gas inlet tube, there is added 750 ml. of dry toluene, and 225 g. (1.5 mole) of piperonal. The resulting solution is stirred, cooled in an ice bath and treated with a stream of methylamine gas until the solution is saturated. To this solution there is added 300 g. of Linde Molecular Sieves Type 3A and the resulting mixture is stirred for about 12 hours at room temperature. The molecular sieves are filtered off and the filtrate concentrated in vacuo on a rotary evaporator to give piperonal-N-methylimine; b.p. 100 to 103° C. at 1.5 mm.

Following the above procedure and using in place of methylamine an equivalent amount of ethylamine there is obtained
(a) piperonal-N-ethylimine.

Also following the above procedure and using in place of piperonal an equivalent amount of
(b) 3,4-dimethoxybenzaldehyde,
(c) p-methoxybenzaldehyde,
(d) m-methoxybenzaldehyde,
(e) p-chlorobenzadlehyde,
(f) m-chlorobenzaldehyde,
(g) p-fluorobenzaldehyde, or
(h) 3-methyl-4-methoxybenzaldehyde
there is obtained
(b) 3,4-dimethoxybenzyl-N-methylimine
(c) p-methoxybenzyl-N-methylimine,
(d) m-methoxybenzyl-N-methylimine,
(e) p-chlorobenzyl-N-methylimine,
(f) m-chlorobenzyl-N-methylimine,
(g) p-fluorobenzyl-N-methylimine, or (h) 3-methyl-4-methoxybenzyl-N-methylimine, respectively.

EXAMPLE 2.

1-Methyl-2-(3,4-methylenedioxyphenyl)-6-oxonipecotic acid.

To a flask equipped with a condenser there is added 100 g. (0.61 mole) of piperonal-N-methylimine, 70 g. (0.61 mole) of glutaric anhydride in 600 ml. of dry xylene. The resulting mixture is refluxed for 4 hours. During the 4 hours, a solution occurred followed by the formation of a copious precipitate. After cooling to room temperature, the solid is filtered off and then dissolved in 700 ml. of methanol and 1000 ml. of methylene chloride. The resulting solution is treated with charcoal, filtered through celite and then concentrated in vacuo to about 400 ml. The resulting solid is then filtered off and washed with a methylene chloride/diethyl ether mixture to give 1-methyl-2-(3,4-methylenedioxyphenyl)-6-oxonipecotic acid; m.p. 231 to 232° C.

Following the above procedure and using in place of piperonal-N-methylimine an equivalent amount of
(a) piperonal-N-ethylimine,
(b) 3,4-dimethoxybenzyl-N-methylimine,
(c) p-methoxybenzyl-N-methylimine,
(d) m-methoxybenzyl-N-methylimine,
(e) p-chlorobenzyl-N-methylimine,
(f) m-chlorobenzyl-N-methylimine,
(g) p-fluorobenzyl-N-methylimine, or
(h) 3-methyl-4-methoxybenzyl-N-methylimine
there is obtained
(a) 1-ethyl-2-(3,4-methylenedioxyphenyl)-6-oxonipecotic acid; m.p. 202° to 204° C.,
(b) 1-methyl-2-(3,4-dimethoxyphenyl)-6-oxonipecotic acid; m.p. 167° to 169° C.,
(c) 1-methyl-2-(p-methoxyphenyl)-6-oxonipecotic acid; m.p. 183° to 185° C.,
(d) 1-methyl-2-(m-methoxyphenyl)-6-oxonipecotic acid; m.p. 117° to 118° C.,
(e) 1-methyl-2-(p-chlorophenyl)-6-oxonipecotic acid; m.p. 219° to 221° C.,
(f) 1-methyl-2-(m-chlorophenyl)-6-oxonipecotic acid;
(g) 1-methyl-2-(p-fluorophenyl)-6-oxonipecotic acid; m.p. 184° to 186° C., or
(h) 1-methyl-2-(3-methyl-4-methoxyphenyl)-6-oxonipecotic acid, respectively.

Also following the above procedure and using in place of glutaric anhydride an equivalent amount of
(i) succinic anhydride,
there is obtained
(i) 2-(3,4-methylenedioxyphenyl)-1-methyl-5-oxo-3-pyrrolidine carboxylic acid; m.p. 211° to 213° C.

Again following the above procedure and using in place of piperonal-N-methylimine an equivalent amount of
(j) 3,4-dimethoxybenzyl-N-methylimine,
(k) p-methoxybenzyl-N-methylimine,
(l) m-methoxybenzyl-N-methylimine,
(m) p-chlorobenzyl-N-methylimine,
(n) m-chlorobenzyl-N-methylimine,
(o) p-fluorobenzyl-N-methylimine, or
(p) 3-methyl-4-methoxybenzyl-N-methylimine, and using in place of glutaric anhydride an equivalent amount of succinic anhydride there is obtained
(j) 2-(3,4-dimethoxyphenyl)-1-methyl-5-oxo-3-pyrrolidine carboxylic acid; m.p. 217° to 218° C.,
(k) 2-(p-methoxyphenyl)-1-methyl-5-oxo-3-pyrrolidine carboxylic acid; m.p. 176° to 181° C.,
(l) 2-(m-methoxyphenyl)-1-methyl-5-oxo-3-pyrrolidine carboxylic acid; m.p. 160° to 162° C.,
(m) 2-(p-chlorophenyl)-1-methyl-5-oxo-3-pyrrolidine carboxylic acid; m.p. 208° to 210° C.,
(n) 2-(m-chlorophenyl)-1-methyl-5-oxo-3-pyrrolidine carboxylic acid,
(o) 2-(p-fluorophenyl)-1-methyl-5-oxo-3-pyrrolidine carboxylic acid; m.p. 155° to 157° C.,
(p) 2-(3-methyl-4-methoxyphenyl)-1-methyl-5-oxo-3-pyrrolidine carboxylic acid; m.p. 183° to 187° C., respectively.

EXAMPLE 3.

1-Methyl-2-(3,4-methylenedioxyphenyl)-3-piperidinemethanol (compounds Ib).

To a flask equipped with stirrer, dropping funnel and under a nitrogen atmosphere there is added 4.8 g. (0.126 mole) of lithium aluminum hydride to 250 ml. of anhydrous tetrahydrofuran. The resulting suspension is stirred and treated dropwise with a solution of 10.0 g. (0.036 mole) of 1-methyl-2-(3,4-methylenedioxyphenyl)-6-oxonipecotic acid in anhydrous tetrahydrofuran at such a rate that reflux occurs. The mixture is then stirred and refluxed for about 24 hours, cooled in an icebath and treated successively with 5 ml. of saturated sodium chloride solution, 5 ml. of 15% sodium hydroxide and 15 ml. of water and after separation stirred for an additional 2 hours. The resulting solid is filtered off and washed with tetrahydrofuran. The combined filtrates are then concentrated to yield 1-methyl-2-(3,4-methylenedioxyphenyl)-3-piperidinemethanol as an oil. The product is then dissolved in anhydrous methanol and saturated with dry hydrogen chloride gas. The solution is then concentrated to about 12 ml. and approximately 60 ml. of diethyl ether is then added. After stirring for 2 hours at room temperature the resultant solid is filtered off to give the hydrochloride salt of the title compound; m.p. 198° to 200° C.

Following the above procedure and using in place of 1-methyl-2-(3,4-methylenedioxyphenyl)-6-oxonipecotic acid an equivalent amount of
(a) 1-ethyl-2-(3,4-methylenedioxyphenyl)-6-oxonipecotic acid,
(b) 1-methyl-2-(3,4-dimethoxyphenyl)-6-oxonipecotic acid,
(c) 1-methyl-2-(p-methoxyphenyl)-6-oxonipecotic acid;
(d) 1-methyl-2-(m-methoxyphenyl)-6-oxonipecotic acid,
(e) 1-methyl-2-(p-chlorophenyl)-6-oxonipecotic acid,
(f) 1-methyl-2-(m-chlorophenyl)-6-oxonipecotic acid,
(g) 1-methyl-2-(p-fluorophenyl)-6-oxonipecotic acid,
(h) 1-methyl-2-(3-methyl-4-methoxyphenyl)-6-oxonipecotic acid,
(i) 2-(3,4-methylenedioxyphenyl)-1-methyl-5-oxo-3-pyrrolidine carboxylic acid,
(j) 2-(3,4-dimethoxyphenyl)-1-methyl-5-oxo-3-pyrrolidine carboxylic acid,
(k) 2-(p-methoxyphenyl)-1-methyl-5-oxo-3-pyrrolidine carboxylic acid,
(l) 2-(m-methoxyphenyl)-1-methyl-5-oxo-3-pyrrolidine carboxylic acid
(m) 2-(p-chlorophenyl)-1-methyl-5-oxo-3-pyrrolidine carboxylic acid,
(n) 2-(m-chlorophenyl)-1-methyl-5-oxo-3-pyrrolidine carboxylic acid, (o) 2-(p-fluorophenyl)-1-methyl-5-oxo-3-pyrrolidine carboxylic acid, or
(p) 2-(3-methyl-4-methoxyphenyl)-1-methyl-5-oxo-3-pyrrolidine carboxylic acid there is obtained
(a) 1-ethyl-2-(3,4-methylenedioxyphenyl)-3-piperidinemethanol hydrochloride; m.p. 222° to 224° C. (base may also be prepared in accordance with the above reaction scheme),
(b) 1-methyl-2-(3,4-dimethoxyphenyl)-3-piperidinemethanol; m.p. 107° to 108° C., (the hydrochloride salt may also be prepared in accordance with the above reaction scheme),
(c) 1-methyl-2-(p-methoxyphenyl)-3-piperidinemethanol as an oil,
(d) 1-methyl-2-(m-methoxyphenyl)-3-piperidinemethanol as an oil,
(e) 1-methyl-2-(p-chlorophenyl)-3-piperidinemethanol; b.p. 110° to 115° C. at 0.25 mm.
(f) 1-methyl-2-(m-chlorophenyl)-3-piperidinemethanol,
(g) 1-methyl-2-(p-fluorophenyl)-3-piperidinemethanol hydrochloride; m.p. 167° to 170° C., (base may also be prepared in accordance with the following reaction scheme),
(h) 1-methyl-2-(3-methyl-4-methoxyphenyl)-3-piperidinemethanol,
(i) 1-methyl-2-(3,4-methylenedioxyphenyl)-3-pyrrolidinemethanol hydrochloride; m.p. 200° to 203° C., (base may also be prepared),
(j) 1-methyl-2-(3,4-dimethoxyphenyl)-3-pyrrolidinemethanol; m.p. 100° to 102° C., (the hydrochloride salt may also be prepared in accordance with the above reaction scheme),
(k) 1-methyl-2-(p-methoxyphenyl)-3-pyrrolidinemethanol as an oil,
(l) 1-methyl-2-(m-methoxyphenyl)-3-pyrrolidinemethanol; b.p. 115° to 120° C. at 0.2 mm.,
(m) 1-methyl-2-(p-chlorophenyl)-3-pyrrolidinemethanol hydrochloride; m.p. 136° to 137° C., (base may also be prepared in accordance with the above reaction scheme),
(n) 1-methyl-2-(m-chlorophenyl)-3-pyrrolidinemethanol,
(o) 1-methyl-2-(p-fluorophenyl)-3-pyrrolidinemethanol hydrochloride; m.p. 156° to 158° C., (base may also be prepared), or
(p) 1-methyl-2-(3-methyl-4-methoxyphenyl)-3-pyrrolidinemethanol; b.p. 150° to 160° C. at 0.2 mm, respectively.

The (±)-1-methyl-2-(3,4-methylenedioxyphenyl)-3-piperidinemethanol isomers of this example may be separated into the following isomers using conventional techniques
1. (+)-cis-1-methyl-2-(3,4-methylenedioxyphenyl)-3-piperidinemethanol.
2. (−)-cis-1-methyl-2-(3,4-methylenedioxyphenyl)-3-piperidinomethanol.
3. (+)-trans-1-methyl-2-(3,4-methylenedioxyphenyl)-3-piperidinemethanol.
4. (−)-trans-1-methyl-2-(3,4-methylenedioxyphenyl)-3-piperidinemethanol.

The remaining title compounds (a) to (p) of this example may also be separated into the isomers illustrated above by conventional techniques.

It will be understood that compounds (a) to (p) of this example have the same isomeric forms as specifically set forth for the title compound.

EXAMPLE 4.

2-(3,4-dimethoxyphenyl)-3-(morpholinomethyl)-1-methylpyrrolidine. (compounds Ia).

STEP (a) 2-(3,4-dimethoxyphenyl)-1-methyl-5-oxo-3-pyrrolidinecarbomorpholide.

To a flask equipped with a stirrer and condenser there is added 60.0 g. (0.22 mole) of 2-(3,4-dimethoxyphenyl)-1-methyl-5-oxo-3-pyrrolidine carboxylic acid to 145 ml. of thionyl chloride. The resulting mixture is stirred at room temperature for about 24 hours. The excess thionyl chloride is then removed in vacuo to give 75.3 g. of crude acid chloride as an oil. The crude acid chloride is not isolated but employed in situ in the preparation of compounds (II).

25.0 g. (0.07 mole) of crude acid chloride is then dissolved in 250 ml. of dry tetrahydrofuran, then cooled in an icebath and treated dropwise with a solution of 6.9 g. (0.077 mole) of morpholine in 50 ml. of tetrahydrofuran. The resulting mixture is stirred overnight at room temperature and then concentrated in vacuo on a rotary evaporator to give a brown oil. The resulting oil is dissolved in 200 ml. of methylene chloride, washed with 100 ml. of 2 N sodium hydroxide, dried over anhydrous magnesium sulfate, filtered and concentrated in vacuo to give 2-(3,4-dimethoxyphenyl)-1-methyl-5-oxo-3-pyrrolidine carbomorpholide.

Following the above procedure and using in place of 2-(3,4-dimethoxyphenyl)-1-methyl-5-oxo-3-pyrrolidine carboxylic acid an equivalent amount of:
(a) 2-(3,4-methylenedioxyphenyl)-1-methyl-5-oxo-3-pyrrolidine carboxylic acid,
(b) 1-ethyl-2-(3,4-methylenedioxyphenyl)-6-oxonipecotic acid,
(c) 1-methyl-2-(3,4-dimethoxyphenyl)-6-oxonipecotic acid, or
(d) 1-methyl-2-(3,4-methylenedioxyphenyl)-6-oxonipecotic acid
there is obtained
(a) 2-(3,4-methylenedioxyphenyl)-1-methyl-5-oxo-3-pyrrolidinecarbomorpholide,
(b) 1-ethyl-2-(3,4-methylenedioxyphenyl)-6-oxonipecotic acid morpholide,
(c) 1-methyl-2-(3,4-methylenedioxyphenyl)-6-oxonipecotic acid morpholide, respectively.

Also following the above procedure and using in place of morpholine an equivalent amount of
(e) ammonia,
(f) dimethylamine,
(g) piperidine,
(h) N-methylpiperazine, or
(i) pyrrolidine
there is obtained
(e) 2-(3,4-dimethoxyphenyl)-1-methyl-5-oxo-3-pyrrolidinecarboxamide,
(f) 2-(3,4-dimethoxyphenyl)-1-methyl-5-oxo-3-pyrrolidine-N,N-dimethyl carboxamide,
(g) 2-(3,4-dimethoxyphenyl)-1-methyl-5-oxo-3-pyrrolidinecarbopiperidide,
(h) 2-(3,4-dimethoxyphenyl)-1-methyl-5-oxo-3-pyrrolidinecarbo-N-methylpiperazide, or
(i) 2-(3,4-dimethoxyphenyl)-1-methyl-5-oxo-3-pyrrolidinecarbopyrrolidide, respectively STEP (b) 2-(3,4-dimethoxyphenyl)-3-(morpholinomethyl)-1-methylpyrrolidine.

To a flask equipped with stirrer, condenser, gas inlet tube and dropping funnel there is added 2.0 g. (0.052 mole) of lithium alunimum hydride to 25 ml. of anhydrous tetrahydrofuran. The resulting mixture is treated dropwise under a nitrogen atmosphere with a solution of 9.0 g. (0.026 mole) of 2-(3,4-dimethoxyphenyl)-1-methyl-5-oxo-3-pyrrolidine carbomorpholide in 25 ml. anhydrous tetrahydrofuran and heated to reflux for about 18 hours. The mixture is then cooled in an icebath and treated dropwise with 4.0 ml. of 2 N sodium hydroxide and 6.0 ml. of water. After stirring for about 1 hour, 5 g. of anhydrous magnesium sulfate is added, the mixture is then filtered and the filtrate concentrated in vacuo to give an oil. The oil is then distilled in a Kügelrohr apparatus to give 2-(3,4-dimethoxyphenyl)-3-(morpholinomethyl)-1-methylpyrrolidine; b.p. 165° to 185° C. at 0.5 mm.

Following the above procedure and using in place of 2-(3,4-dimethoxyphenyl)-1-methyl-5-oxo-3-pyrrolidinecarbomorpholide an equivalent amount of (a) 2-(3,4-methylenedioxyphenyl)-1-methyl-5-oxo-3-pyrrolidinecarbomorpholide,
(b) 1-ethyl-2-(3,4-methylenedioxyphenyl)-6-oxonipacotic acid morpholide,
(c) 1-methyl-2-(3,4-dimethoxyphenyl)-6-oxonipecotic acid morpholide, or
(d) 1-methyl-2-(3,4-methylenedioxyphenyl)-6-oxonipecotic acid morpholide there is obtained
(a) 2-(3,4-methylenedioxyphenyl)-3-(morpholinomethyl)-1-methylpyrrolidine,
(b) 2-(3,4-methylenedioxyphenyl)-3-(morpholinomethyl)-1-ethylpiperidine,
(c) 2-(3,4-dimethoxyphenyl)-3-(morpholinomethyl)-1-methylpiperidine, or
(d) 2-(3,4-methylenedioxyphenyl)-3-(morpholinomethyl)-1-methylpiperidine, respectively.

Also following the above procedure and using in place of 2-(3,4-dimethoxyphenyl)-1-methyl-5-oxo-3-pyrrolidine carbomorpholide an equivalent amount of (e) 2-(3,4-dimethoxyphenyl)-1-methyl-5-oxo-3-pyrrolidinecarboxamide,
(f) 2-(3,4-dimethoxyphenyl)-1-methyl-5-oxo-3-pyrrolidine-N,N-dimethylcarboxamide,
(g) 2-(3,4-dimethoxyphenyl)-1-methyl-5-oxo-3-pyrrolidinecarbopiperidide,
(h) 2-(3,4-dimethoxyphenyl)-1-methyl-5-oxo-3-pyrrolidinecarbo-N-methylpiperazide, or
(i) 2-(3,4-dimethoxyphenyl)-1-methyl-5-oxo-3-pyrrolidinecarbopyrrolidide
there is obtained (e) 2-(3,4-dimethoxyphenyl)-3-(aminomethyl)-1-methylpyrrolidine,
(f) 2-(3,4-dimethoxyphenyl)-3-(N,N-dimethylaminomethyl)-1-methylpyrrolidine,
(g) 2-(3,4-dimethoxyphenyl)-3-(piperidinomethyl)-1-methylpyrrolidine,
(h) 2-(3,4-dimethoxyphenyl)-3-(4-methylpiperazinomethyl)-1-methylpyrrolidine, or
(i) 2-(3,4-dimethoxyphenyl)-3-(pyrrolidinomethyl)-1-methylpyrrolidine, respectively.

What is claimed is:

1. A compound of the formula

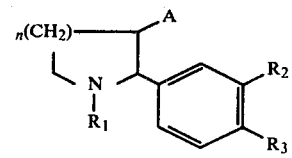

wherein
A is —CH$_2$OH, and
R$_1$ is hydrogen or lower alkyl having 1 to 2 carbon artoms, i.e., methyl or ethyl, and
R$_2$ and R$_3$ together represent methylenedioxy, and
n is 1 or 2, ora pharmaceutically acceptable acid addition salt thereof.

2. The compound of claim 1 which is 1-methyl-2-(3,4-methylenedioxyphenyl)-3-piperidinemethanol.

3. The compound of claim 1 which is 1-methyl-2-(3,4-methylenedioxyphenyl)-3-piperidinemethanol hydrochloride.

4. The compound of claim 1 which is 1-ethyl-2-(3,4-methylenedioxyphenyl)-3-piperidinemethanol.

5. The compound of claim 1 which is 1-ethyl-2-(3,4-methylenedioxyphenyl)-3-piperidinemethanol hydrochloride.

6. The compound of claim 1 which is 1-methyl-2-(3,4-methylenedioxyphenyl)-3-pyrrolidinemethanol.

7. The compound of claim 1 which is 1-methyl-2-(3,4-methylenedioxyphenyl)-3-pyrrolidinemethanol hydrochloride.

8. A method of treating lipidemia which comprises administering to a mammal in need of said treatment a hypolipidemically effective amount of a compound of claim 1.

9. A pharmaceutical composition for use in the treatment of lipidemia which comprises an effective amount of a compound of claim 1 and a pharmaceutically acceptable diluent or carrier therefor.

* * * * *

UNITED STATES PATENT AND TRADEMARK OFFICE
CERTIFICATE OF CORRECTION

PATENT NO. : 4,219,560                           Page 1 of 2

DATED : August 26, 1980

INVENTOR(S) : WILLIAM J. HOULIHAN

It is certified that error appears in the above—identified patent and that said Letters Patent is hereby corrected as shown below:

Col. 1, between lines 25 to 30, after the word "or" add the formula --

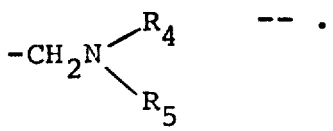

-- .

Col. 1, lines 36 to 38 should be inserted above the formulas set out on line 30.

Col. 1, delete the formula set out between lines 40 to 45.

Col. 1, line 56 after the word "is" insert the formula -- $-CH_2N\begin{smallmatrix}R_4\\R_5\end{smallmatrix}$ -- and insert the words --are prepared according to the following reaction scheme -- .

UNITED STATES PATENT AND TRADEMARK OFFICE
CERTIFICATE OF CORRECTION

PATENT NO. : 4,219,560

DATED : August 26, 1980

INVENTOR(S) : WILLIAM J. HOULIHAN

It is certified that error appears in the above—identified patent and that said Letters Patent is hereby corrected as shown below:

Col. 2, delete lines 12 and 13 and the formula

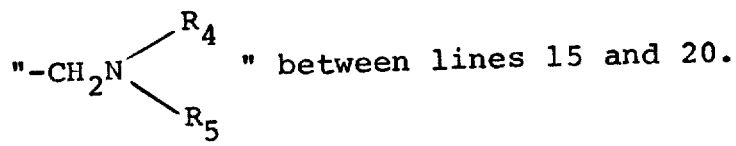

" between lines 15 and 20.

Signed and Sealed this

Tenth Day of November 1981

[SEAL]

Attest:

GERALD J. MOSSINGHOFF

Attesting Officer

Commissioner of Patents and Trademarks